United States Patent [19]

Yoneta et al.

[11] 4,290,972

[45] Sep. 22, 1981

[54] PROCESS FOR THE PRODUCTION OF 4-AMINOBUTYRIC ACID OR ITS DERIVATIVES

[75] Inventors: Toshio Yoneta, Yokohama; Seiji Shibahara, Tokyo; Shigeo Seki, Tokyo; Shunzo Fukatsu, Tokyo, all of Japan

[73] Assignee: Meiji Seika Kaisha, Ltd., Tokyo, Japan

[21] Appl. No.: 92,940

[22] Filed: Nov. 9, 1979

Related U.S. Application Data

[63] Continuation-in-part of Ser. No. 805, Jan. 4, 1979, abandoned.

[30] Foreign Application Priority Data

Jan. 25, 1978 [JP] Japan ................................. 53-6142

[51] Int. Cl.$^3$ ................... C07C 99/10; C07C 121/42; C07C 121/453
[52] U.S. Cl. .......................... 260/465 B; 260/465.2; 560/159; 562/561; 562/567; 562/553
[58] Field of Search ...................... 562/553, 561, 567; 260/465.2, 465 B; 560/159

[56] References Cited

U.S. PATENT DOCUMENTS

| | | | |
|---|---|---|---|
| 2,417,749 | 3/1947 | Hagemeyer | 260/465.2 |
| 2,839,547 | 6/1958 | Berther | 562/553 |
| 3,031,490 | 4/1962 | Ferris | 562/561 |
| 3,062,869 | 11/1962 | Gould | 562/553 |
| 3,217,027 | 11/1965 | Little | 260/465.2 |
| 3,255,248 | 6/1966 | Suessenguth | 562/553 |
| 3,354,203 | 11/1967 | Little | 562/561 |
| 3,928,445 | 12/1975 | Rogic | 562/561 |

OTHER PUBLICATIONS

Thompson, J. Am. Chem. Soc., 73, pp. 5841-5846 (1951).

*Primary Examiner*—Natalie Trousof
*Assistant Examiner*—Michael Shippen
*Attorney, Agent, or Firm*—Haight, Rosfeld & Noble

[57] ABSTRACT

4-Amino-2-hydroxybutyric acid or 2,4-diaminobutyric acid may be readily produced by a new process comprising reacting a propionic acid compound containing a β-carboxamido substituent (-CONH$_2$) on the carbon atom at the 3-position and optionally containing hydroxyl substituent and protected or unprotected amino substituent on the α-carbon atom thereof, with an alkanoic acid anhydride in liquid pyridine to convert the carboxamido group into a nitrile group, with occasional acylation of a α-hydroxyl group, occasionally removing the alkanoyl group from the α-acyloxyl group of the resulting nitrile intermediate, and then reducing the resultant nitrile compound with hydrogen to convert the nitrile group into an aminomethyl group, and further optionally removing the residual amino-protecting group from the resultant 4-aminobutyric acid compound.

10 Claims, No Drawings

PROCESS FOR THE PRODUCTION OF 4-AMINOBUTYRIC ACID OR ITS DERIVATIVES

This application is a new continuation-in-part application of the patent application Ser. No. 805 filed Jan. 4, 1979, now abandoned, which is now pending.

BACKGROUND OF THE INVENTION

1. Field of the Invention

This invention relates to a new process for the production of a 4-aminobutyric acid or its derivatives from a 3-carboxamido-propionic acid or its derivative. More particularly, this invention relates to a new chemical process of producing 4-aminobutyric acid or its derivatives by utilizing a novel chemical reaction which has now been discovered by the present inventors during their researches of the chemical conversion of a primary carboxamido group into nitrile group.

Heretofore, various processes of converting a primary carboxamido group

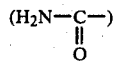

into a nitrile group were known, including the method of treating the carboxamido group with dicyclohexyl-carbodi-imide (B. Liberek et al., "Tetrahedron" 22, 2303 (1966)); the method of treating the carboxamido group with thionyl chloride (C. Ressler et al., "Journal of Organic Chemistry" 36, 3960 (1971)); the method of treating the carboxamido group with tosyl chloride (M. Zaoral et al., "Coll. Czech. Chem. Comm." 24, 1993 (1952)); and the method of treating the carboxamido group with trifluoroacetic acid anhydride (F. Campagna et al., "Tetrahedron Letters" No. 21, 1813 (1977)). However, all of these prior art methods suffer from many disadvantages in that the reagents employed therein are expensive, in that the reaction conditions for the conversion are severe and vigorous, and/or in that there is a need to use such a protected derivative of the starting compound of which the carboxyl group and/or amino group has or have been protected by suitable protective groups, in order to prevent any undesired side-reaction during the conversion.

SUMMARY OF THE INVENTION

We, the present inventors, has extensively researched in an attempt to provide a new and economic route by which 4-aminobutyric acid or its derivatives can be produced in a facile way starting from a propionic acid compound containing a primary carboxamido substituent on the carbon atom at the 3-position of the propionic acid compound. As a result, we have now found that the carboxamido group present in the starting propionic acid compound employed may readily be converted into a nitrile group with great efficiency even at ambient temperature by reacting with an alkanoic acid anhydride such as acetic anhydride, in a reaction medium consisting essentially of liquid pyridine. This reaction of the carboxamido group of an aliphatic compound with an alkanoic acid anhydride in pyridine to convert the same into a nitrile group was not previously known and is considered to be a new chemical reaction.

Further research of this new chemical reaction has revealed that the starting compound employed for this reaction should necessarily contain the free carboxylic group the molecule thereof in addition to the carboxamido group in order to achieve the desired conversion of the carboxamido group into the nitrile group, and also that the intramolecular distance between both the carboxyl group and the carboxamido group of the starting compound is very important in achieving the desired conversion with success, which means that the carboxamido group must be positioned at such a distance from the carboxyl group of the starting propionic acid compound that is just sufficient to allow these two functional groups to be combined together so as to form one isoimide ring and a preferably five-membered or six-membered iso-imido ring. With this new chemical reaction, many advantages are obtained that inexpensive and readily available reagents can be used; that the starting propionic acid compound employed may optionally contain a hydroxyl substituent without the necessity of protecting the hydroxyl group; that the reaction of the starting propionic acid compound with an alkanoic acid anhydride proceeds rapidly even at ambient temperature; and that the carboxamido group of the starting compound can be converted into a nitrile group with great efficiency, rendering the present process to be a practical and commercially profitable one.

DETAILED DESCRIPTION OF THE INVENTION

According to the present invention, therefore, there is provided a process for the production of a 4-aminobutyric acid derivative represented by the formula (I):

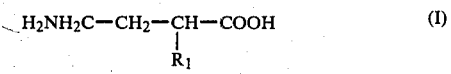

wherein $R_1$ is a hydrogen atom, hydroxyl group or a protected amino group, which comprises the steps of:

(a) reacting a starting propionic acid compound represented by the formula (II):

wherein $R_1$ is as defined above, with an alkanoic acid anhydride of the formula (III):

wherein $R_2$ is an alkyl group of 1-6 carbon atoms, in a reaction medium essentially consisting of liquid pyridine, to convert the carboxamido group into a nitrile group and produce the nitrile compound represented by the formula (V):

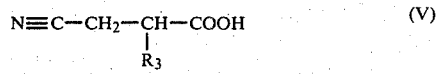

wherein $R_3$ is a hydrogen atom, an alkanoyloxy group $R_2CO.O-$ or a protected amino group same as $R_1$, (b) occasionally hydrolyzing the resultant nitrile compound (V) to remove the alkanoyl group $R_2CO-$ from said nitrile compound (V) when this nitrile compound contains the alkanoyloxy group $R_2CO.O-$ which is formed by acylation of the 2-hydroxyl group with the alkanoic acid anhydride (III) if the 2-hydroxyl group is present in the starting propionic acid compound (II), whereby there is produced the nitrile compound of the formula (V')

$$N\equiv C-CH_2-CH(R_1)-COOH \qquad (V')$$

wherein $R_1$ is as defined above, (c) reducing the resultant nitrile compound (V) to convert the nitrile group into an aminomethyl group and produce the 4-aminobutyric acid derivative of the formula (I).

If desired, the present process may be followed by a step (d) of removing the residual amino-protecting group from the resulting 4-aminobutyric acid compound of the formula (I).

According to a particular embodiment of the present invention, there is provided a process for the production of 4-amino-2-hydroxybutyric acid of the formula (I'):

$$H_2NCH_2-CH_2-CH(OH)-COOH \qquad (I')$$

which comprises the steps of:

(a) reacting a propionic acid compound of the formula (II'):

$$H_2NOC-CH_2-CH(OH)-COOH \qquad (II')$$

with an alkanoic acid anhydride of the formula (III):

$$(R_2CO)_2O \qquad (III)$$

wherein $R_2$ is an alkyl group of 1–6 carbon atoms, in a reaction medium essentially consisting of liquid pyridine, to convert the carboxamido group into a nitrile group and thereby produce the nitrile compound of the formula (V''):

$$N\equiv C-CH_2-CH(O-OCR_2)-COOH \qquad (V'')$$

wherein $R_2$ is as defined above, (b) hydrolyzing the resulting nitrile compound (V'') to remove the alkanoyl group $R_2CO-$ therefrom and to produce the nitrile compound of the formula (V')

$$N\equiv C-CH_2-CH(OH)-COOH \qquad (V')$$

(c) and then reducing the nitrile compound (V') with hydrogen to convert the nitrile group into an aminomethyl group and produce the 4-aminobutyric acid compound of the formula (I'):

$$H_2N-CH_2-CH_2-CH(OH)-COOH \qquad (I')$$

In the step (a) of the process according to the present invention, in general, the starting propionic acid compound (II) or (II') is reacted with an alkanoic acid anhydride (III) in the reaction medium essentially consisting of liquid pyridine which may preferably be dry.

In this step (a), the reaction may be carried out at ambient temperature, but, if desired, may be conducted also at an elevated temperature up to a boiling point of the solvent employed. Preferred reaction temperature is 20°–25° C. The reaction time required may usually be in a range of 1–3 hours.

Suitable examples of the starting propionic acid compound (II) include 3-carboxamido-propionic acid; L-2-amino-3-carboxamido-propionic acid (known as L-asparagine) and its amino-protected derivatives; and L-2-hydroxy-3-carboxamido-propionic acid (known as L-malamidic acid). When the starting propionic acid compound (II) employed contains an amino substituent other than the amino group present in the carboxamido group, this amino group must be previously protected with any known amino-protecting group. On the other hand, when a starting propionic acid compound (II) has a hydroxyl substituent, it is not necessary to protect this hydroxyl group of the starting compound, though this hydroxyl group can be acylated by the alkanoic acid anhydride in the step (a) of the present process. Any of the known amino-protecting groups including an aralkyloxycarbonyl group such as carbobenzoxyl and an alkoxycarbonyl group such as tert-butoxycarbonyl may be used for this purpose. The amino-protecting group is preferably one that can easily be removed from the amino-protected nitrile compound during the subsequent reduction step of the present process. For example, a carbobenzoxyl group as the amido-protecting group is most preferable as it is easily removable by hydrogenolysis at the same time as when the reduction step (c) of the present process is conducted with the nitrile product (V) or (V').

When a starting propionic acid compound (II) is such one containing as the value of $R_1$ an amino group protected with an amino-protecting goup, this amino-protected derivative of the starting compound may be prepared by reacting said starting compound with a substantially equimolar proportion of a known reagent for introduction of the amino-protecting group which is usually employed according to the conventional synthesis of peptides. The amino-protecting group-introducing reagent may be, for example, a chloroformate of the formula:

$$Cl-CO-OR_4$$

wherein $R_4$ is an alkyl group of 1–5 carbon atoms such as methyl, ethyl, t-butyl and t-amyl; a cycloalkyl group of 3–6 carbon atoms such as a cyclopentyl and cyclohexyl; an aralkyl group such as phenyl-alkyl group containing alkyl of 1–4 carbon atoms, such as benzyl and p-nitrobenzyl; an aryl group such as phenyl; or a heterocyclic group such as furfuryl, or a p-nitrophenyl carbonate of the formula:

$$p-NO_2-C_6H_5-O-CO-OR_4$$

or an N-hydroxysuccinimide ester of the formula:

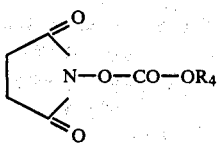

or an azidoformate of the formula:
$N_3—CO—OR_4$ wherein $R_4$ is as defined above. This reagent may be reacted with a starting compound containing the free amino group in a suitable solvent such as water, ethanol, acetone or a mixture thereof under neutral or basic conditions in a manner known in the prior art for the synthesis of peptides.

The acid anhydride of the formula (III) to be used is preferably acetic anhydride, but propionic anhydride and butyric anhydride may also be used.

The acid anhydride (III) is preferably used at a ratio of 1 mol or more per mol of the starting compound (II) or (II') used.

When the step (a) of the present process is performed using the starting propionic acid compound (II) where $R_1$ is hydroxyl (namely, the propionic acid compound of the formula (II')), the 2-hydroxyl group as $R_1$ is acylated by the alkanoic acid anhydride (III) to form the nitrile compound (V) containing the 2-alkanoyloxy group $R_2CO.O—$. Accordingly, in this case, the step (b) of hydrolytically removing the alkanoyl group $R_2CO—$ from that nitrile compound to restore the free 2-hydroxyl group is interposed before the step (c) of reducing the nitrile compound is conducted. The hydrolytic removal of the alkanoyl group from the 2-alkanoyloxy group is conducted by reacting the nitrile compound with hydrochloric acid or sulfuric acid or aqueous alkali or aqueous ammonia in a manner known in the technique of de-protecting a protected hydroxyl group.

When the step (a) of the present process is carried out using the starting compound (II) where $R_1$ is a protected amino group, the reaction mixture of this step (a) is then immediately concentrated by distilling off the pyridine under reduced pressure, and the concentrated solution is admixed with hydrochloric acid, usually leading to the precipitation of the nitrile product of the formula (V) where $R_1$ is amino group. While, when the step (a) of the present process is conducted using the propionic acid compound (II) where $R_1$ is hydroxyl group, the reaction mixture of the step (a) may be concentrated by distilling off the pyridine under reduced pressure and the concentrated solution so obtained is subjected to acidic or alkaline hydrolysis as the step (b) for the hydrolytic removal of the alkanoyl group from the 2-alkanoyloxy group intermediately formed, followed by the step (c) for the reductive conversion of the nitrile group into aminomethyl group.

The reduction of the nitrile compound (V) or (V') in the step (c) of the present process may be achieved according to any conventional hydrogenation procedure by which the nitrile group can be converted into an aminomethyl group. It is preferred that the nitrile compound (V) or (V') should be catalytically reduced with hydrogen in the presence of a hydrogenation catalyst such as platinum oxide and palladium.

Moreover, the removal of the residual amino-protecting group from the 4-aminobutyric acid compound so produced may be carried out in the step (d) by a conventional procedure, if necessary. For example, the above amino-protecting groups may be removed by weak acid hydrolysis or by hydrogenolysis simultaneously to the above catalytic reduction of the second step.

By utilizing the process of the present invention, biochemically valuable compounds, L-2,4-diaminobutyric acid and L(−)-4-amino-2-hydroxybutyric acid may readily be produced. Particularly, L(−)-4-amino-2-hydroxybutyric acid is one of the important reagents for producing various derivatives of aminoglycosidic antibiotics, since it has been found in recent years that L(−)-4-amino-2-hydroxybutyric acid may be reacted with certain aminoglycosidic antibiotics such as kanamycin A, B, C or ribostamycin to give therapeutically useful semi-synthetic antibiotics which are highly active against a wide variety of aminoglycosidic antibiotics-resistant bacteria (see U.S. Pat. No. 4,008,362, for example).

According to the process of the present invention, for example, N-carbobenzoxy-L-asparagine, the compound of the formula (II) where $R_1$ is the group $—NHCOOCH_2—C_6H_5$, is treated with acetic anhydride in pyridine at room temperature for one hour, pyridine is then distilled off from the reaction mixture under reduced pressure, the concentrated reaction solution is processed under acidic conditions with hydrochloric acid to crystallize the N-carbobenzoxy-$\beta$-cyano-L-alanine formed. This intermediate nitrile product is subsequently reduced with hydrogen in the presence of a catalyst of platinum oxide by the conventional hydrogenation procedure to convert the cyano (nitrile) group of the intermediate product into an aminomethyl group and simultaneously to remove the carbobenzoxy group (the amino-protecting group), and finally the resultant deprotected product is purified by a suitable method such as recyrstallization. In this way, L-2,4-diaminobutyric acid is readily produced in a high yield of 75% starting from L-asparagine. Further, L(−)-4-amino-2-hydroxybutyric acid can be produced starting from this L-2,4-diaminobutyric acid (Agr. Biol. Chem. 40, 8, 1649–1650 (1976)). Preparation of L-malamidic acid from L-asparagine may be conducted by the method described in Agr. Biol. Chem. 40 8, 1651–1652 (1976).

Moreover, the process of the present invention may be carried out starting with L-malamidic acid, the compound of the formula (II) where $R_1$ is a hydroxyl group. In this case, L(−)-4-amino-2-hydoxybutyric acid may be obtained in a yield of 61% at most without the need to isolate the intermediate nitrile product.

Thus, the present process provides a new route which is advantageous in that all the reagents employed in each step are inexpensive, the reaction of each step may be conducted under moderate reaction conditions, no undesired isomerization reaction occurs, and no optical resolution treatment of the final product is required. So the present process is a practical and very useful one.

The present invention is now illustrated with reference to the following Examples.

EXAMPLE 1

(1) Synthesis of N-carbobenzoxy-$\beta$-cyano-L-alanine 2.66 g (10 millimole) of N-carbobenzoxy-L-asparagine (Journal of Organic Chemistry, 26, 3356–3360

(1961)) was admixed with 30 ml of dry pyridine and 1.2 ml (12 millimole) of acetic anhydride, and the admixture obtained was stirred at a temperature from 20° to 25° C. for one hour. The reaction solution was then concentrated to a syrup by distilling off pyridine under reduced pressure, and the residue was diluted with 50 ml of 1 N hydrochloric acid. The product deposited as colorless needles was collected by filtration, washed with cold water and dried to afford 2.05 g of N-carbobenzoxy-$\beta$-cyano-L-alanine. Yield 83%. This product was found to have the following properties:

$[\alpha]_D^{25} - 18.7°$ (c=1.27, methanol).

Melting point 129°-131.5° C.

(2) Production of L(+)-2,4-diaminobutyric acid 1.24 g (5 millimole) of N-carbobenzoxy-$\beta$-cyano-L-alanine was dissolved in a mixture of 80 ml of ethanol, 20 ml of water and 3 ml of concentrated hydrochloric acid, the resulting solution was admixed with 100 mg of platinum oxide, and the admixture was subjected to reduction with hydrogen at 3 atm. at room temperature for five hours. By this procedure, the amino-protecting group (the carbobenzoxy group) was also removed from the amino-protected compound, simultaneously to the catalytic reduction of the cyano group into aminomethyl group. The reaction mixture was filtered to remove the catalyst and then washed with water. The washings were combined with the filtrate and the combined liquid was neutralized by addition of an aqueous solution of 1 N sodium hydroxide. The resulting neutralized solution was the passed through a column of 40 ml of cation-exchange resin, Amberlite CG-50 (NH$_4$-form) (a product of Rohm & Haas Co., U.S.A.) for the adsorption of the desired product. After the column was washed with 120 ml of water, it was eluted with 0.3 N aqueous ammonia. The eluate was collected in 10 ml-fractions and fractions Nos. 1-13 combined was concentrated to dryness, affording 558 mg of L(+)-2,4-diaminobutyric acid. Yield 95%.

This substance was taken up in 10 ml of 1 N hydrochloric acid and admixed with ethanol to precipitate the desired product as colorless crystals. This product was found to have the following properties:

Melting point 193°-194° C.

$[\alpha]_D^{25} + 13.4°$ (c=1.25, water).

EXAMPLE 2

Production of L(−)-4-amino-2-hydroxybutyric acid 532 mg (4 millimole) of L-malamidic acid (NH$_2$CO—CH$_2$—CH(OH)—COOH) was admixed with 15 ml of dry pyridine and 1.5 ml of acetic anhydride, and the resultant admixture was stirred at room temperature for one hour. The reaction solution was then concentrated to a syrup by distilling off pyridine under reduced pressure, and the resulting syrup was dissolved in a mixture of 20 ml of ethanol and 5 ml of water added to the syrup itself. To this solution (containing 3-cyano-2-acetyloxypropionic acid formed) were further added 1 ml of concentrated hydrochloric acid and 50 mg of platinum oxide, and the mixture was subjected to the hydrolytic removal of the 2-acetyl group and to the reduction with hydrogen at 3 atm. at room temperature overnight. The reaction mixture was filtered to remove the catalyst and washed with water. The washings were combined with the filtrate and the combined solution was concentrated to dryness under reduced pressure. The solid residue so obtained was taken up in 10 ml of water, and the resulting solution was then passed through a column of 20 ml of cation-exchange resin, Dowex 50W×4 (H$^+$-form) (a product of Dow Chemical Co., U.S.A.) for the adsorption of the desired product. After the column was washed with 100 ml of water, it was eluted with 0.5 N aqueous ammonia. The resultant eluate was collected in 5 ml-fractions and fraction Nos. 15-20 combined were concentrated to dryness, affording 291 mg of L(−)-4-amino-2-hydroxybutyric acid. Yield 61%. This product was recrystallized from water-methanol for purification. The crystalline product obtained was found to have the following properties:

Melting point 197°-198.5° C.

$[\alpha]_D^{25} - 28.2°$ (c=1.2, water).

EXAMPLE 3

Production of L-4-amino-2-hydroxybutyric acid (1) Preparation of L-malamidic acid from L-asparagine L-asparagine monohydrate (13.5 g, 90 millimol) was dissolved in 136 ml of 20% aqueous acetic acid and to the resulting solution which was cooled to 5° C. was added dropwise a solution of 9.2 g (133 millimol) of sodium nitrite (NaNO$_2$) in 45 ml of water. The admixture was allowed to stand at ambient temperature overnight to effect the conversion of the 2-amino group of L-asparagine into a hydroxyl group. The reaction mixture was admixed with 2.0 ml of ethylene diamine to decompose the excessive amount of sodium nitrite, and the mixture was charged to a column of 300 ml of a cation-exchange resin (available as "Diaion PK-216" from Mitsubishi Kasei Co., Japan) (H$^+$ form). The resin column was then eluted with water, and the eluate was collected in fractions. The fractions containing L-malamidic acid which could be confirmed by a silica gel thin layer chromatography developed with n-butanol-acetic acid (25:1), giving a spot at Rf=0.11 (colored with Bromcresol Green) were combined together and the combined solution (totally 400 ml) was concentrated to 5 ml under reduced pressure.

(2) Preparation of 3-cyano-2-hydroxypropionic acid

The concentrate containing L-malamidic acid obtained in the above procedure (1) was admixed with 150 ml of pyridine, and the admixture was concentrated to 10 ml under reduced pressure by distilling off the water content and pyridine. The concentrate so obtained was admixed with 120 ml of pyridine and 33 ml of acetic anhydride, followed by allowing to stand for one hour at ambient temperature. The reaction mixture containing L-3-cyano-2-acetoxypropionic acid product which could be confirmed by a silica gel thin layer chromatography developed with n-butanol-acetic acid (25:1), giving a spot at Rf=0.23 (colored by Bromcresol Green) was concentrated to 30 ml, followed by admixing with 50 ml of methanol and 60 ml of concentrated aqueous solution of ammonium hydroxide. The admixture was allowed to stand for 30 minutes at ambient temperature to effect the removal of the acetyl group.

(3) Production of L-4-amino-2-hydroxylbutyric acid

The reaction solution obtained in the above procedure (2) and containing L-3-cyano-2-hydroxylpropionic acid was concentrated to 30 ml under reduced pressure and then admixed with 40 ml of acetic acid, 160 ml of water and 1.1 g of platinum oxide. The admixture was then subjected to hydrogenation with hydrogen under atmospheric pressure and at ambient temperature for 4 hours. The reaction mixture was filtered to remove the catalyst and the catalyst was washed with water. The filtrate and the washings were combined and passed through a column of 400 ml of Diaion PK-216 (H+ form), followed by washing with 1500 ml of water. The resin column was then eluted with 2 N aqueous ammonia. The eluate fractions containing L-4-amino-2-hydroxybutyric acid were combined together (totally 320 ml) and concentrated to 80 ml, followed by admixing with 240 ml of ethanol. The admixture was left at 5° C. overnight, giving a crystalline product. This product was removed by filtration, washed with ethanol and then dried in vacuo to obtain 5.35 g of L-4-amino-2-hydroxybutyric acid. Yield 50%, as calculated from the L-asparagine used.

What we claim is:

1. A process for preparing a nitrile compound of the formula

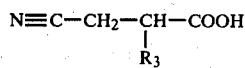

wherein $R_3$ is hydrogen, $R_2COO-$ wherein $R_2$ is alkyl of 1-6 carbon atoms, or a protected amino group $R_1$, which comprises reacting a propionic acid compound of the formula

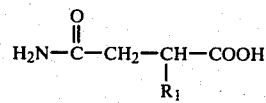

wherein $R_1$ is hydrogen, hydroxyl, or a protected amino group, with an alkanoic acid anhydride of the formula $(R_2CO)_2O$ wherein $R_2$ has the above-indicated values in a liquid reaction medium consisting essentially of pyridine to form said nitrile compound.

2. A process according to claim 1, wherein $R_1$ is hydroxyl.

3. A process according to claim 2, further comprising hydrolyzing the nitrile compound to remove the alkanoyl group $R_2COO-$ therefrom and produce a nitrile compound of the formula

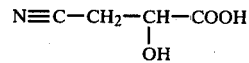

4. A process according to claim 2, further comprising reducing the resultant nitrile product with hydrogen to form the corresponding 4-amino-2-hydroxybutyric acid derivative.

5. A process according to claim 8, wherein $R_1$ is hydrogen.

6. A process according to claim 5, further comprising reducing the resultant nitrile compound to form the corresponding 4-aminobutyric acid derivative.

7. A process according to claim 1, wherein $R_1$ is an amino-protecting group.

8. A process according to claim 7, wherein $R_1$ is carbobenzoxyl.

9. A process according to claim 7, further comprising reducing the nitrile compound so obtained with hydrogen to convert the nitrile group into an aminomethyl group and produce a corresponding amino protected 2,4-diaminobutyric acid derivative.

10. A process according to claim 9, further comprising removing the amino-protecting groups to form the corresponding 2,4-diaminobutyric acid derivative.

* * * * *